United States Patent [19]

MacLeay et al.

[11] 4,010,152
[45] Mar. 1, 1977

[54] ALIPHATIC ALPHA-(HYDROPEROXY) AZO COMPOUNDS AND SALTS THEREOF

[75] Inventors: Ronald Edward MacLeay, Williamsville; Chester Stephen Sheppard, Tonawanda, both of N.Y.

[73] Assignee: Pennwalt Corporation, Philadelphia, Pa.

[22] Filed: Mar. 21, 1974

[21] Appl. No.: 453,445

Related U.S. Application Data

[63] Continuation-in-part of Ser. No. 88,249, Nov. 9, 1970, abandoned, which is a continuation-in-part of Ser. No. 725,180, April 29, 1968, abandoned, which is a continuation-in-part of Ser. No. 616,158, Feb. 15, 1967, abandoned.

[52] U.S. Cl. .............................. 260/192; 260/152; 260/156; 260/865; 526/218
[51] Int. Cl.$^2$ .................................... C07C 107/02
[58] Field of Search ............ 260/192, 610 R, 610 A

[56] References Cited

UNITED STATES PATENTS

| | | | |
|---|---|---|---|
| 3,135,615 | 6/1964 | Higashzuchi | 260/610 R X |
| 3,282,912 | 11/1966 | Benzing | 260/192 X |
| 3,449,217 | 6/1969 | Harvey | 260/610 R X |

OTHER PUBLICATIONS

Huttel et al., Ber. Devt. Chem., vol. 89, 1956, pp. 2644–2647.
Elkobaisi et al., J. Chem. Soc. (London), vol. OF1958, pp. 2431–2432.

Primary Examiner—Charles F. Warren
Attorney, Agent, or Firm—Barry A. Bisson

[57] ABSTRACT

New aliphatic azo compounds containing an α-hydroperoxy group and the alkali metal and alkaline earth metal salts thereof as represented by the general structure

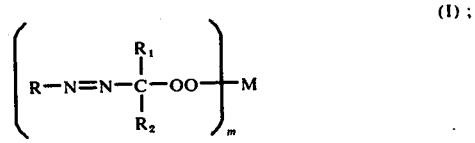

processes for preparing I where M is H and R is t-aliphatic by reacting t-aliphatic azo compounds having an α-halo substituent with about an equimolar amount of sodium or hydrogen peroxide; processes for converting I where M is H to its alkali or alkaline earth metal salt by reaction with aqueous solutions of the corresponding base or with calcium or sodium hydride; and the use of these novel compounds as polymerization initiators for vinyl monomers and as curing agents for resins. For example, 2-t-butylazo-2-hydroperoxy-4-methylpentane is prepared from sodium peroxide and 2-t-butylazo-2-chloro-4-methylpentane and used to polymerize vinyl chloride and to cure unsaturated polyester resin.

9 Claims, No Drawings

ALIPHATIC ALPHA-(HYDROPEROXY) AZO COMPOUNDS AND SALTS THEREOF

CROSS-REFERENCE TO RELATED APPLICATIONS

This application is a continuation-in-part of copending application Ser. No. 88,249 filed Nov. 9, 1970 now abandoned, which in turn is a continuation-in-part of Ser. No. 725,180 filed Apr. 29, 1968 (now abandoned), which in turn is a continuation-in-part application of application Ser. No. 616,158, filed Feb. 15, 1967 (now abandoned).

BACKGROUND OF THE INVENTION

This disclosure relates to novel alkyl, cycloalkyl and aralkyl azo compounds containing an $\alpha$-hydroperoxy group, and the alkali metal or alkaline earth metal salts thereof; to processes for their preparation; and to their use as polymerization initiators for ethylenically unsaturated monomers and as curing agents for polyester resin compositions.

To the best of applicants' knowledge, there are no known examples of aliphatic-azo compounds as defined by structure I. Aromatic-azoalkanes containing $\alpha$-hydroperoxy groups are reported in R. Criegee and G. Lohaus, Chem. Ber. 84, 219 (1951); and in F. Minisci, Gazz. Chim. ital. 89, 626 (1959). K. H. Pausacker, J. Chem. Soc., 3478 (1950); A. J. Bellamy and R. D. Guthrie, J. Chem. Soc. 2788 (1965); G. J. Karabatsos et al., J.A.C.S., 85, 3627 (1963); and H. C. Yas et al., J. Org. Chem. 30, 2832 (1965) have studied auto-oxidation of arylhydrazones.

U.S. Pat. No. 3,278,304 describes a process for the photopolymerization of ethylenically unsaturated organic compositions, using azo-hydroperoxides as initiators. While only aromatic azo-hydroperoxides (derived from aromatic hydrazones) are used in the working examples, they state that aliphatic azo-hydroperoxides are suitable and that "all these azohydroperoxides are manufactured according to known methods." Applicants, however, do not know of the previous existence of any such aliphatic azohydroperoxides or of any known method for their preparation. Since aromatic azo compounds are normally much more stable than the corresponding aliphatic azo compounds which are highly susceptible to decomposition, it is submitted that the subject patent does not give sufficient information to suggest how such compounds might be prepared.

BRIEF SUMMARY OF THE INVENTION

This invention relates to

A. New aliphatic azo-hydroperoxides containing an $\alpha$-hydroperoxy group and the alkali metal and alkaline earth metal salts thereof:

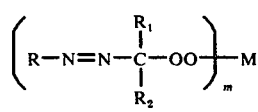

where:

M is hydrogen, alkali metal (e.g. sodium, potassium, lithium) or alkaline earth metal (e.g. calcium, barium, magnesium);

m is the valence of M;

R is a $C_1$ to $C_{12}$ alkyl, $C_3$ to $C_{12}$ cyclo-, bicyclo- or tricycloalkyl, or $C_7$ to $C_9$ aralkyl radical;

$R_1$ and $R_2$ are separately selected from hydrogen and a $C_1$ to $C_8$ alkyl, $C_3$ to $C_{12}$ cyclo-, bicyclo- or tricycloalkyl, $C_7$ to $C_{12}$ aralkyl, $C_6$ to $C_{14}$ aryl or 5 to 6 membered heterocyclic radical wherein the hetero atom is O, S or N (i.e., as in furan, pyran, pyridine, pyrrole, thiophan or thiophen) or, taken together, $R_1$ and $R_2$ can form a $C_3$ to $C_7$ alkylene diradical (i.e., together with their common carbon atom, they form $C_4$–$C_8$ cycloalkyl); and one or more of each of R, $R_1$ and $R_2$ can be substituted with lower (i.e., about 1–4 carbons) alkoxy, hydroxy, carboxy, lower alkoxycarbonyl, lower acyloxy (i.e., lower alkylcarbonyloxy), halogen (i.e., chlorine, bromine, fluorine or iodine), cyano, amido (as in dimethylamido) or lower alkylsulfonato radicals;

B. A method for preparing

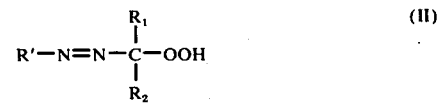

by reacting about equimolar amounts of a tertiary-aliphatic $\alpha$-halo-azo-compound,

and sodium peroxide (or hydrogen peroxide in the presence of an acid acceptor), where $R_1$ and $R_2$ are as defined above, X is chlorine or bromine and R' is the same as R above where R is a $C_4$ to $C_{12}$ t-aliphatic (alkyl, cycloalkyl or aralkyl) radical (i.e., the R carbon attached to the azo group must be a tertiary carbon);

C. A process for preparing I where M is alkali metal or alkaline earth metal by contacting I where M is H (i) with at least an equivalent molar amount (preferably equivalent or slight excess) of a cold (preferably 0° to 15° C.) aqueous solution of the corresponding inorganic base, or (ii with about an equivalent molar amount of sodium or calcium hydride;

D. The use of I as a polymerization initiator (free radical generator) for homo- or copolymerization of ethylenically unsaturated monomers which are responsive at suitable temperatures to free radical generators, especially for initiating vinyl chloride polymerizations in the 10°–60° C. temperature range; and E. The use of I as a curing agent (free radical initiator) for the curing of unsaturated polyester resin compositions in the presence of the novel I compounds, especially for curing unsaturated polyester-vinyl monomer blends at temperatures of 20°–90° C., preferably near room temperatures.

DETAILED DESCRIPTION OF INVENTION

In addition to the compounds (I) and methods set forth herein, other compounds, e.g., 2-(t-butylazo)-2-cyano-4-methyl-4-methoxypentane, and preparatory methods are described in our application Ser. No. 725,180, filed Apr. 29, 1968, which is now abandoned in favor of Ser. Nos. 88,249, 88,247, 88,110, 88,109, and 88,250 all filed Nov. 9, 1970 and all now abandoned and Ser. No. 88,120 filed Nov. 9, 1970 (issued May 21, 1974 as U.S. Pat. No. 3,812,094).

PREPARATION OF II

The above-described reaction of tertiary-aliphatic α-halo-azo compounds (III) with sodium (or hydrogen) peroxide is run in inert solvents such as ether, tetrahydrofuran, water, alcohols (above $C_3$), aqueous alcohols and formamides). When alcohols are used as solvent, the $C_1$–$C_3$ alcohols should not be used since they react with the α-haloazo (III) to form alkoxy derivatives. The reaction can be run at 0°–50° C., but preferably is run at 10°–25° C. to obtain a practical reaction rate and a minimum of decomposition. The α-haloazo compound should be added slowly to the peroxide solution to prevent formation of the symmetrical peroxide which occurs when the α-haloazo compound is present in greater than a 1:1 molar ratio to the peroxide. III can be added neat (as is) or in a solution of an inert solvent such as ether, hydrocarbons, chlorinated hydrocarbons or $C_4$ or higher alcohols.

Novel compounds I (including II) have low thermal stability, making them excellent low temperature free radical initiators, but also making them very hazardous if not properly refrigerated upon storage. Unlike non-peroxidic azo compounds, compounds I are subject to induced decomposition and are very sensitive to contamination by acids, metal ions and reducing agents. In addition, some of these compounds (for example, where R is t-butyl and $R_1$ and $R_2$ are methyl) are very sensitive to shock in the pure form.

It is preferred to prepare the novel I compounds in hydrocarbon solvents at concentrations of around 30–70%. At these concentrations one still has a practical concentration of I in the solvent and has reduced the safety hazards tremendously. Moreover the I compound is still generally soluble in the solvent at the recommended storage temperature. As the structure of the I compound varies, the solubility of the I compound varies and adjustment of the concentration is required in some cases to keep the product in solution.

PREPARATION OF SALTS OF I

When converting I where M is H to the corresponding metal salts by stirring with cold aqueous solutions of base, the hydroperoxide (I) is preferably added to the aqueous basic solution slowly with stirring so that the temperature can be easily controlled. While any of the inorganic bases such as sodium, potassium, lithium, magnesium, calcium or barium hydroxide can be used, sodium and potassium hydroxide are preferred.

The sodium and calcium salts can also be easily prepared and isolated by reacting a hydrocarbon or ether solution of the hydroperoxide (I) with equivalent amounts of sodium or calcium hydride. After preparation of the salts, they can be separated from the hydrocarbon or ether solvent by filtration and stored under refrigerated conditions.

UTILITY

These new compounds (I) are free radical generators, polymerization initiators for vinyl monomers, curing agents for polyester resins, initiators for free radical initiated chemical reactions, blowing agents for producing foamed polymers and plastics, selective oxidizing agents and organic intermediates for a variety of reactions such as preparing other azo-peroxides, e.g. azo-peresters and generators of reactant free radicals.

It has been observed that these new compositions are initiators for the polymerization or copolymerization of unsaturated monomers such as alkenes, vinyl halides, vinyl esters, vinylidene halides and alkenyl aromatics.

Illustrative polymerizable monomers are ethylene, vinyl chloride, vinylidene chloride, vinyl acetate, vinylpyridine, vinylpyrrolidone, vinylcarbazole, butadiene, isoprene, acrylonitrile, acrylic acid, acrylic acid esters, methacrylic acid, methacrylic acid esters, styrene, chlorostyrene, methylstyrenes and in the high pressure polymerization of ethylene.

It is a further advantage of these compounds that many of these polymerizations can be carried out at room temperature or below without needing any activators or co-catalysts present. This is especially true in the case of vinyl chloride. In addition, these compounds are very efficient polymerization initiators. Specific illustrations are given in the working examples.

These compounds are also very efficient curing agents of polyester resins, even at very low levels of catalyst concentration, at room temperature. The cured polyester resins are water-white or off-white in color compared to the reddish-brown resin obtained with previously disclosed phenylazohydroperoxides. Specific illustrations of this utility are given in the working examples as well as comparative data obtained with phenylazohydroperoxides and other peroxides disclosed in the art.

Unsaturated polyesters which are used as the one component of the polyester resin compositions according to the present invention are, for instance, polyesters as they are obtained by esterifying preferably ethylenically unsaturated di-or polycarboxylic acid or their anhydrides, such as maleic acid, fumaric acid, glutaconic acid, itaconic acid, mesaconic acid, citraconic acid, allyl malonic acid, allyl succinic acid, and others, with saturated or unsaturated polyalcohols such as ethylene glycol; diethylene glycol (2,2′-dihydroxy ethyl ether); triethylene glycol (ethylene glycol bis(2-hydroxy ethyl ether); propanediol-1,2; butanediol-1,3; 2,2-dimethyl propanediol-1,3; butene (2)-diol-1,4, glycerol, pentaerythritol, mannitol, and others. Mixtures of such acids and/or alcohols may also be used. The unsaturated di- or polycarboxylic acids may be replaced, at least partly, by saturated carboxylic acids such as adipic acid, succinic acid, sebacic acid, hydrophthalic acid, and others and their anhydrides such as phthalic anhydride. The acids used as well as the alcohols employed may be substituted by other substituents, preferably by halogen. Examples of suitable halogenated acids are, for instance, tetrachloro phthalic acid; 1,4,5,6,7,7-hexachloro bicyclo (2,2,1) heptene (5)-2,3-dicarboxylic acid, and others, or their anhydrides.

The other component of the unsaturated polyester resin compositions are unsaturated monomers, preferably ethylenically unsaturated monomers such as styrene, vinyl toluene, methyl methacrylate, diallyl phthalate, dibutyl fumarate, acrylonitrile, triallyl cyanurate, α-methyl styrene, divinyl benzene, methyl acrylate, diallyl maleate, n-butyl methacrylate, ethyl acrylate, and others, which are copolymerizable with said polyesters.

A preferred resin composition contains as the polyester component the esterification product of propylene glycol (a polyalcohol), maleic anhydride (anhydride of an unsaturated dicarboxylic acid) and phthalic anhydride (anhydride of an aromatic dicarboxylic acid) and as the monomer component styrene.

The novel I compounds evolve one mole of nitrogen gas per mole when they are decomposed. In addition, other gases are evolved from the breakdown and/or disproportionation of the radicals formed. Thus, compounds I are also useful in applications where copious quantities of gases are desired, such as in producing foamed polymers.

COMPOUNDS

Many novel compounds of the present invention are taught in the examples to follow. Additional compounds which can be prepared according to this invention include:

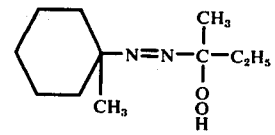

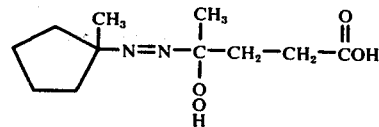

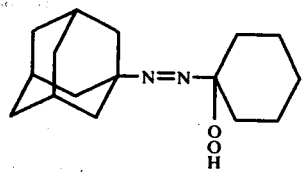

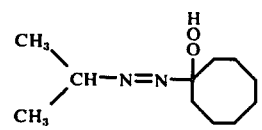

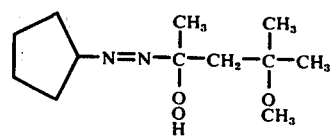

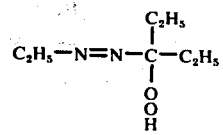

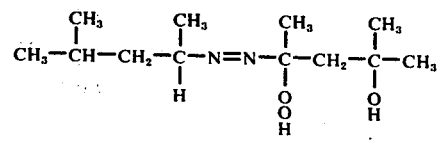

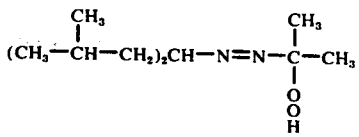

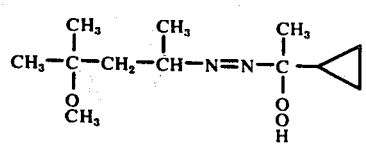

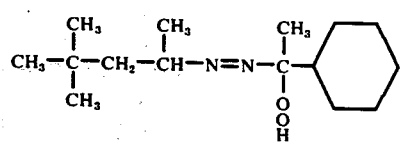

-continued
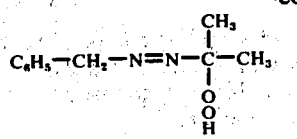
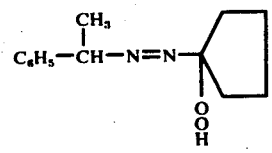
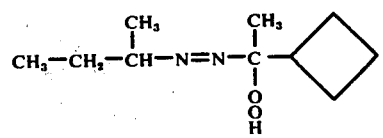
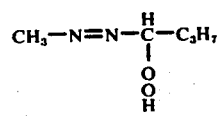
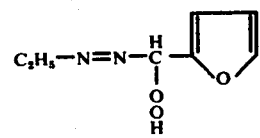
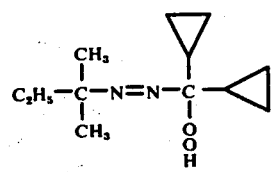
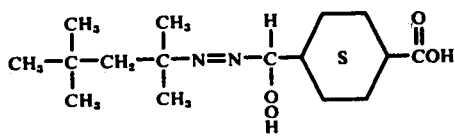
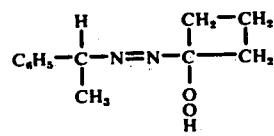
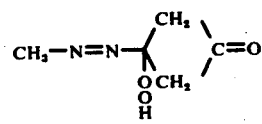
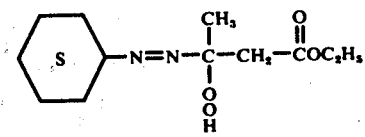
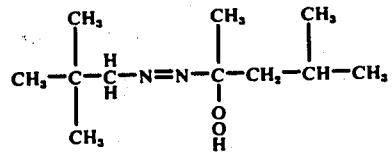

-continued
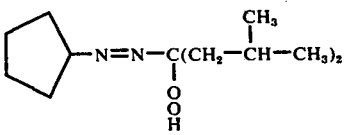
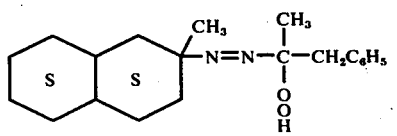
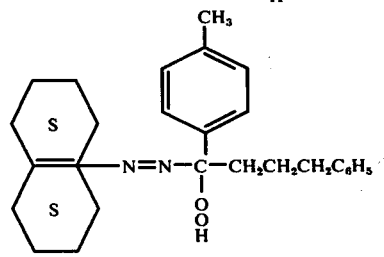
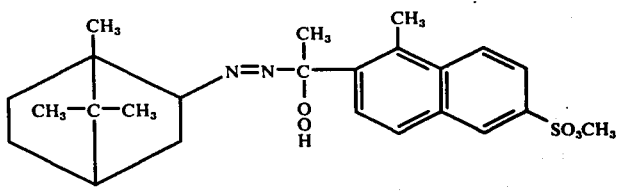
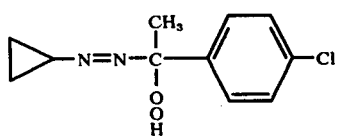
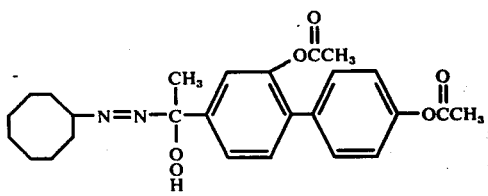
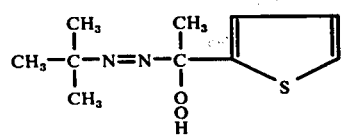
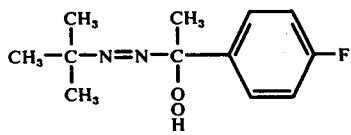
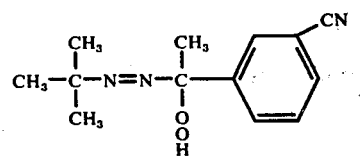
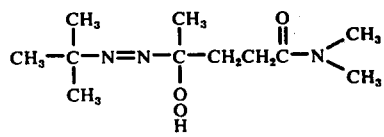

-continued
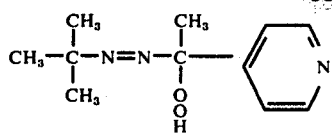
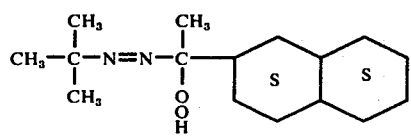
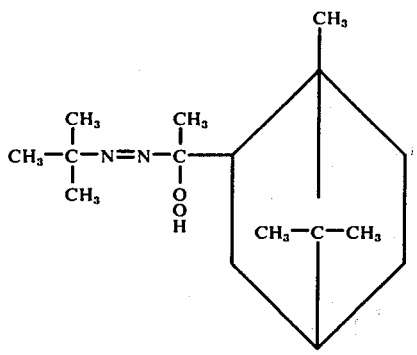
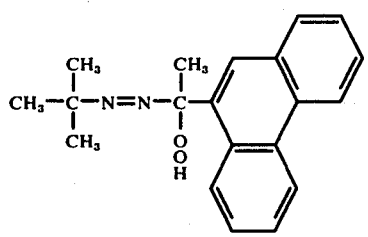
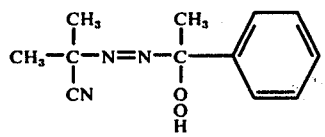
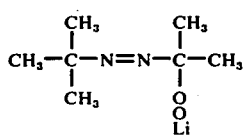
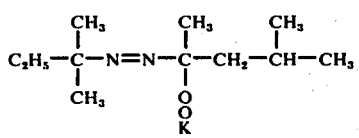
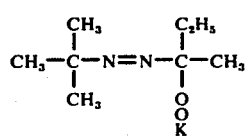
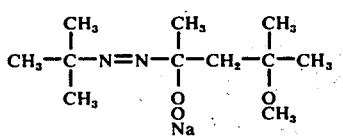
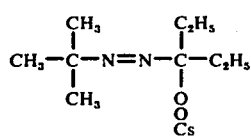
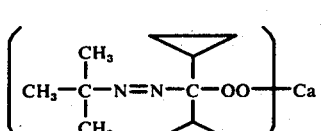
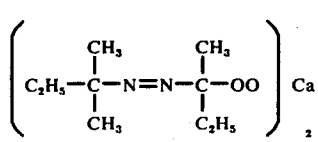
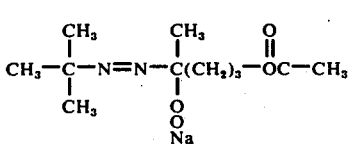

-continued

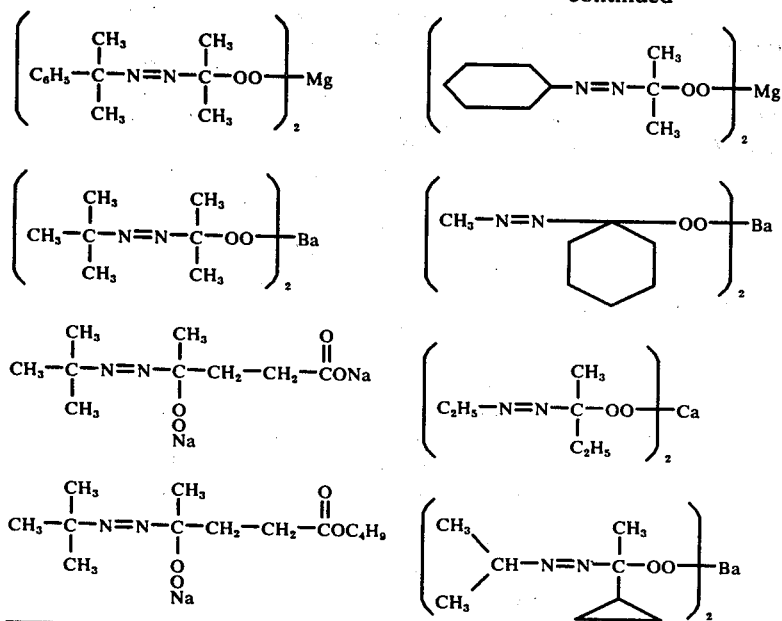

EXAMPLES

The following examples illustrate the invention but in no way limit the scope thereof.

EXAMPLE I

Preparation of
2-t-butylazo-2-hydroperoxy-4-methylpentane

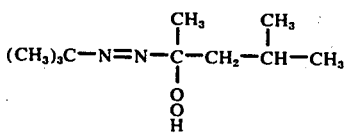

To a stirred solution of 1.56g (.02 moles) of sodium peroxide in 30 ml. of 75% aqueous methanol in a 50 ml. erlenmeyer flask immersed in a cold water bath, was added 4.1g (.02 moles) of 2-t-butylazo-2-chloro-4-methylpentane dropwise. After the addition was complete, the reaction mixture was stirred for an additional 45 minutes and poured into ice water containing 0.02 moles of HaSO$_4$. The product was extracted with pentane and washed with cold solutions of ammonium sulfate and sodium bicarbonate, washed with water, dried over anhydrous sodium sulfate, filtered and the pentane stripped off under reduced pressure while the flask was immersed in an ice bath. The yield was 2.7 grams (67% of theory) and the product began to decompose when allowed to warm to room temperature. The infrared spectrum showed the characteristic hydroperoxide absorption at 3300–3400 cm$^{-1}$.

EXAMPLE II

Preparation of
2-t-butylazo-2-hydroperoxy-4-methylpentane

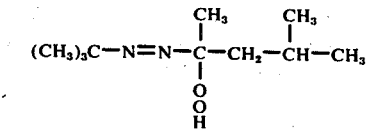

A solution of 50 g of the t-butylhydrazone of methyl isobutyl ketone in 50 grams of odorless mineral spirits was added to a 250 ml. jacketed reactor equipped with a mechanical stirrer, thermometer, condenser, a fitted polyethylene gas inlet tube and a condenser. The solution was warmed to 35° C by circulating warm water through the jacket and with rapid stirring the oxygen was slowly bubbled into the solution. The reaction was monitored by following the disappearance of the t-butylhydrazone by gas chromatography. After the reaction was approximately half complete (1 hour), the temperature was lowered to 20° C and the remainder of the reaction was carried out at this temperature. When the gas chromatographic scan indicated that t-butylhydrazone was completely oxidized (another hour) the solution was cooled at 0° C by circulating ice water through the jacket. The solution was then weighed into a cold polyethylene bottle and stored at −30° C. The yield was 105.3g or 96.5% of theory. The infrared spectrum of the product showed the strong absorbance of the hydroperoxide group at 3300–3400 cm$^{-1}$ and a trace amount of ketone (a decomposition product).

A pure sample of 2-t-butylazo-2-hydroperoxy-4-methylpentane was obtained by low temperature recrystallizations from purified pentane. The pure compound is a low melting solid (below 0° C) and is not shock sensitive at 12 inches (duPont tester).

EXAMPLE III

Curing an Unsaturated Polyester-Styrene Resin with 2-t-Butylazo-2-hydroperoxy-4-methylpentane An unsaturated polyester resin was made by reacting maleic anhydride (1.0 moles), phthalic anhydride (1.0 moles), and propylene glycol (2.2 moles) until an acid number of 45–50 was obtained. To this was added hydroquinone at a 0.013% concentration. Seven parts of this unsaturated polyester was diluted with 3 parts of monomeric styrene to obtain a homogeneous blend having a viscosity of 13.08 poise and a specific gravity of 1.14.

To 20 grams of this blend was added 0.2 grams of a 30% solution of 2-t-butylazo-2-hydroperoxy-4-methylpentane in dodecane and the mixture stirred up well with a wooden spatula. The internal temperature was recorded as a function of time and a peak exotherm of 295° F (146° C) was reached in 13.5 minutes indicating an excellent cure of the unsaturated polyester-styrene resin blend had occurred. The resultant cured material was very hard and was water white in color.

Without an initiator, no cure of this resin blend occurred even after more than 30 minutes at 212° F (100° C). Likewise 2-phenylazo-2-hydroperoxy-4-methylpentane (a compound where R in (I) is phenyl and not covered by this invention) did not cure the resin blend at room temperature. A 1 percent loading of a 33% solution of 2-phenylazo-2-hydroperoxy-4-methylpentane did cure the resin blend to a hard resin in 1.7 minutes at 82° C. This indicates that the phenylazohydroperoxides are higher temperature curing agents. The cured resin had an unattractive brown color however.

EXAMPLE IV

Polymerization of Vinyl Chloride with 2-t-Butylazo-2-hydroperoxy-4-methylpentane 2-t-Butylazo-2-hydroperoxy-4-methylpentane was used as an initiator in the polymerization of vinyl chloride using the well known bottle polymerization technique at autogenous pressures. The formulation used in evaluation is set out below:

| | |
|---|---|
| Vinyl chloride monomer | 100g. |
| Water (distilled) | 210ml. |
| *Methocel (1500 cps) (1% solution) | 20ml. |
| Sorbitan monostearate (1% solution) | 10ml. |
| Polyoxyethylene sorbitan monostearate (1% solution) | 10ml. |
| 2-t-Butylazo-2-hydroperoxy-4-methylpentane | (variable) |

*A hydroxypropyl methylcellulose product of Dow Chemical

A water suspension was prepared as set out in the above formulation and added to a 24-ounce beverage bottle which was then frozen at −20° C. A series of bottles was prepared and varying amounts of the initiator added, followed by the freshly distilled vinyl chloride. The bottles were capped, and placed in a water bath thermostatted at 30° C. The bath was equipped to cause the rotation of the bottles end over end. After the polymerization had continued at 30° C for 16 hours, the bottles were cooled, vented of excess vinyl chloride monomer and the yield of polyvinyl chloride determined gravimetrically. It was found that 0.053 grams of 2-t-butylazo-2-hydroperoxy-4-methylpentane were required per 100 grams of vinyl chloride monomer to obtain a 90% conversion of poly(vinyl chloride).

In contrast, 2-phenylazo-2-hydroperoxy-4-methylpentane (an art compound) gave a maximum conversion to poly(vinyl chloride) of only 7.0% at concentration levels in the range of 0.026 to 0.189 grams per 100 grams of vinyl chloride after 8 hours at 55° C. This compound was evaluated at 55° C because its ten hour half-life is at ≈66° C whereas that of the 2-t-butylazo-2-hydroperoxy-4-methyl-pentane used above is at 34° C.

For comparison, $\alpha,\alpha'$-azobis(isobutyronitrile) (a well known azo compound) which has a ten hour half life at 65° C gave a 90% conversion to poly(vinyl chloride) after 8 hours at 55° C using 0.127 grams per 100 grams of vinyl chloride and 2-(t-butylazo)-2-cyano-4-methyl-4-methoxypentane (disclosed in Ser. No. 725,180) which has a ten hour half life at 55° C gave a 90% conversion to poly(vinyl chloride) in 8 hours at 55° C using 0.051 grams per 100 grams of vinyl chloride.

Thus, the novel I compounds of the present invention are very efficient initiators for vinyl chloride polymerization while the analogous art compounds (i.e. those where R = aryl in structure I) are very ineffective initiators for vinyl chloride.

EXAMPLE V

Preparation of 2-t-butylazo-2-hydroperoxypropane

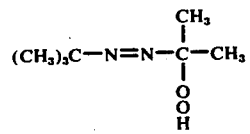

A solution of 10 mls. of acetone t-butylhydrazone in 20 mls. of decane was oxidized by passing dry air through the solution. The reaction was carried out and followed using the same techniques used in Example II. The temperature was kept at 10°–20° C throughout the oxidation and the reaction required 6 hours to go to completion. The final product was not shock sensitive, however when the pure 2-t-butylazo2-hydroperoxypropane was isolated by low temperature recrystallizations it proved to be very sensitive to shock. The product was stored at −30° C.

A 50% solution of acrylonitrile in benzene was polymerized to a solid in a test tube by adding a couple of drops of the above decane solution to it at room temperature.

At a 1.0 weight percent loading the above decane solution cured the unsaturated polyester-styrene resin of Example III at room temperature giving a peak exotherm of 280° F (138° C) in 11.7 minutes and a very hard cured resin which was water white in color.

In the polymerization of vinyl chloride (16 hours at 30° C) as in Example IV, it was found that 0.084 grams of 2-t-butylazo-2-hydroperoxy-4-methylpentane were required per 100 grams of vinyl chloride monomer to obtain a 90% conversion to polyvinyl chloride.

EXAMPLE VI

Preparation of 2-t-Butylazo-2-hydroperoxyoctane

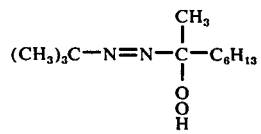

A solution of 10 mls. of the t-butylhydrazone of 2-octanone in 20 mls. of dodecane was oxidized by passing dry air through the solution. The first half of the oxidation was carried out at 35° C for 1 hour (no oxidation occurred at 20° C) and the second half carried out at 25° C for 1 hour using the same techniques and apparatus described in Example II. The pure product was obtained by low temperature recrystallization from purified pentane and was not sensitive to shock. The solution was stored at −30° C.

At a 1.0 weight percent loading the above dodecane solution cured the unsaturated polyester-styrene resin of Example III at room temperature giving a peak exotherm of 292° F (144° C) in 9.2 minutes and a very hard cured resin which was water white in color.

In the polymerization of vinyl chloride (16 hours at 40° C) using the procedure described in Example IV, it was found that 0.025 grams of 2-t-butylazo-2-hydroperoxyoctane were required per 100 grams of vinyl chloride monomer to obtain a 90% conversion to polyvinyl chloride.

EXAMPLE VII

Preparation of 2-t-Butylazo-2-hydroperoxy-4,4-dimethylpentane

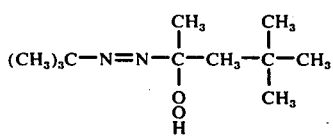

A solution of 10 grams of the t-butylhydrazone of methyl neopentyl ketone in 20 grams of odorless mineral spirits was oxidized by passing oxygen through the solution. No oxidation occurred at 20° C but the oxidation was completely over in 1 hour at 25° C using the same technique and apparatus described in Example II. The solution was stored at −30° C.

At a 1.0 weight percent loading the above mineral spirit solution cured the unsaturated polyester-styrene resin of Example III at room temperature giving a peak exotherm of 268° F (132° C) in 30 minutes and a very hard cured resin which was water white in color.

EXAMPLE VIII

Preparation of 1-t-Butylazo-1-hydroperoxy-cyclohexane

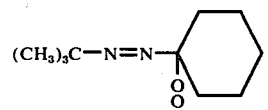

A solution of 80 grams of cyclohexanone t-butylhydrazone in 80 grams of odorless mineral spirits was oxidized by passing oxygen through the solution as in Example II. The solution was heated to 39° C to initiate the oxidation. The reaction was followed by gas chromatography and after the oxidation was about ½ complete (1hour) the temperature was lowered to 25° C and the remainder of the oxidation carried out at this temperature (½ hour). After the cyclohexanone t-butylhydrazone had completely reacted, the reaction was cooled to 0° C by circulating ice water through the jacket. The product was then weighed into a cold poly bottle and stored at −30° C or below. The yield was 171 g (97.7% of theory).

At a 0.67 weight percent loading the above mineral spirit solution cured the unsaturated polyester-styrene resin of Example III at room temperature giving a peak exotherm of 315° F (157° C) in 7.0 minutes and a very hard cured resin which was water white in color.

In the polymerization of vinyl chloride (16 hours at 50° C) using the procedure described in Example IV; it was found that 0.016 grams of 1-t-butylazo-1-hydroperoxycyclohexane were required per 100 grams of vinyl chloride monomer to obtain a 90% conversion to polyvinyl chloride.

1-Phenylazo-1-hydroperoxycyclohexane, an art compound, did not cure the unsaturated polyester-styrene resin of Example III to a hard resin at room temperature but did cure the resin in 1.9 minutes at 82° C indicating that the phenylazohydroperoxides are higher temperature curing agents. The cured resin was a dark reddish brown in color.

EXAMPLE IX

Preparation of 2-t-Butylazo-2-hydroperoxy-4-methoxy-4-methylpentane

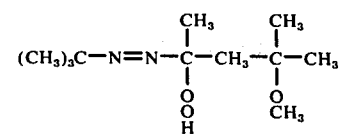

A solution of 60 grams of the t-butylhydrazone of pentoxane (4-methoxy-4-methyl-pentanone-2) in 60 grams of odorless mineral spirits was oxidized by passing oxygen through the solution as in Example II. The oxidation was initiated at 30° C by adding 2 drops of a 50% solution of 2-t-butylazo-2-hydroperoxy-4-methylpentane. The oxidation was ½ complete after 50 minutes at 30° C. The temperature was lowered to 20° C. and an additional 1 hour was required before the oxidation was complete. It was then cooled to 0° C. by circulating ice water through the jacket and weighed into a cold poly bottle and stored at −30° C. or below. The yield was 126 g (97% of theory). The solution is not sensitive to shock.

At a 1.0 weight percent loading the above solution cured the unsaturated polyester-styrene resin of Example III at room temperature giving a peak exotherm of 290° F. (143° C,) in 6.0 minutes and a very hard cured resin which was water white in color.

EXAMPLE X

Preparation of 2-t-Cumylazo-2-hydroperoxyoctane

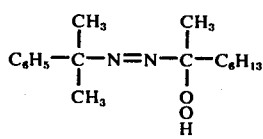

A solution of 4 grams of the t-cumylhydrazone of 2-octanone in 40 mls. of hexane was oxidized by passing oxygen through the solution as in Example II. The oxidation was initiated at 35° C. and the oxidation carried out for 1 hour at 35° C. and then the temperature lowered to 25° C. for an additional hour. The reaction was followed by infrared spectroscopy. At the end of the reaction period the solution was cooled to 0° C., drained into a flask, placed on a rotating evaporator and the hexane stripped off at 0° C. The yield was 3.7g. It was immediately diluted to 50% with decane.

At a 2.0 weight percent loading, the above decane solution cured the unsaturated polyester-styrene resin of Example III at room temperature giving a peak exotherm of 254° F. (123° C) in 30 minutes and a very hard cured resin which was light straw yellow in color.

EXAMPLE XI

Preparation of 2-t-Amylazo-2-hydroperoxy-4-methylpentane

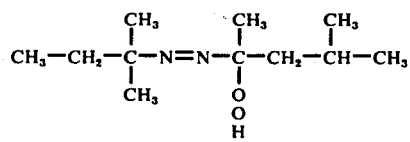

A solution of 9 grams of the t-amylhydrazone of methyl isobutyl ketone in 30 grams of purified hexane was oxidized by passing oxygen through the solution as in Example II. The oxidation was initiated at 38° C and the oxidation carried out for 1 hour at 38° C. At the time the oxidation was about ½ complete, the temperature was lowered to 25° C. The oxidation was complete in 45 minutes, cooled to 0° C, drained into a flask, placed on a rotating evaporator and the hexane stripped off at 0° C until a 50% concentration was obtained. The solution was stored at −30° C.

EXAMPLE XII

Preparation of 1-t-Butylazo-1-hydroperoxyheptane

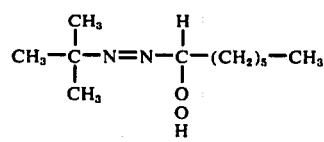

A solution of 20 grams (.109 moles) of the t-butylhydrazone of normal heptanal in 80 grams of odorless mineral spirits was oxidized by passing oxygen through the solution as in Example II. The oxidation was initiated at 37° C and the oxidation carried out for 40 minutes at 37° C at which time the oxidation was complete. The temperature of the solution was lowered to 0° C and the solution drained into a tared, cooled, polyethylene bottle, weighed and stored at −30° C. The solution weighed 100.8 grams (88.5% yield).

At a 2.0 weight percent loading, the above solution cured the unsaturated polyester-styrene resin of Example III at room temperature giving a peak exotherm of 261° F (127° C) in 11.8 minutes and a very hard cured resin which was a light straw yellow in color.

EXAMPLE XIII

Preparation of 1-t-Butylazo-1-phenyl-1-hydroperoxy methane

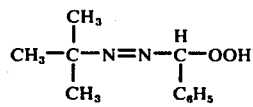

A solution of 20 grams (0.1135 moles) of the t-butylhydrazone of benzaldehyde in 80 grams of odorless mineral spirits was oxidized by passing oxygen through the solution as in Example II. The oxidation was initiated at 35° C and the oxidation carried out for 15 minutes at 35° C. At this point gas chromatography indicated the oxidation was approximately half complete so the temperature was lowered to 25° C and the oxidation continued for another 20 minutes at which time the oxidation was complete. The solution was cooled to 0° and drained into a tared, cooled, polyethylene bottle, weighed and stored at −30° C. The solution weighed 100.2 grams 85.6% yield).

At a 5.0 weight per cent loading, the above solution cured the unsaturated polyester-styrene resin of Example III at room temperature giving a peak exotherm of 195° F (90° C) in 23 minutes. The cured resin was light yellow in color.

EXAMPLE XIV

Preparation of 1-t-Butylazo-1-hydroperoxy-1-phenylethane

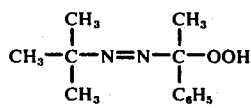

A solution of 10 grams (0.0527 moles) of the t-butylhydrazone of acetophenone in 40 grams of odorless mineral spirits was oxidized by passing oxygen through the solution as in Example II. The oxidation was initiated at 35° C. The reaction was followed by gas chromatography, following the disappearance of the t-butylhydrazone peak. The t-butylhydrazone peak immediately started to decrease so the temperature was lowered to 15°–20° C. The reaction was complete in 35 minutes. The solution was cooled to 0° and drained into a tared, cooled polyethylene bottle, weighed and stored at −30° C. The solution weighed 50.0 grams (86% yield).

At a 2.5 weight percent loading, the above solution cured the unsaturated polyester-styrene resin of Example III at room temperature giving a peak exotherm of 257° F (125° C) in 4.3 minutes and a hard cured resin which was light yellow in color.

EXAMPLE XV

Preparation of 2-Methylazo-2-hydroperoxy-4-methylpentane

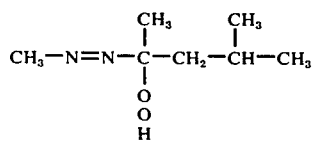

A solution of 20 grams (0.156 moles) of the methylhydrazone of methyl isobutyl ketone in 80 grams of heptane was oxidized by passing oxygen through the solution as in Example II. The oxidation was initiated at 37° C. The reaction was followed by gas chromatography, following the disappearance of the methylhydrazone peak. The reaction was complete in 20 minutes at 37° C. The solution was cooled to 0° C and drained into a tared, cooled, polyethylene bottle, weighed and stored at −30° C. The solution weighed 103 grams (92.5% yield).

At a 2.0 weight percent loading, the above solution cured the unsaturated polyester-styrene resin of Example III at room temperature giving a peak exotherm of 315° F (157° C) in 6.5 minutes and a very hard cured resin which was water white in color.

In the polymerization of vinyl chloride (8 hours at 50° C) using the procedure described in Example IV, it was found that 0.62 grams of 2-methylazo-2-hydroperoxy-4-methylpentane were required per 100 grams of vinyl chloride monomer to obtain a 90% conversion to polyvinyl chloride.

EXAMPLE XVI

Preparation of 2-Cyclohexylazo-2-Hydroperoxypropane

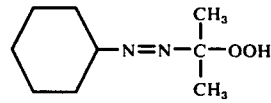

A solution of 5.0 grams (.0324 moles) of acetone cyclohexylhydrazone in 70 grams of heptane was oxidized by passing oxygen through the solution as in Example II. The oxidation was initiated at 35° C. The reaction was followed by gas chromatography, following the disappearance of the cyclohexylhydrazone peak. The reaction was complete in 35 minutes at 35° C. The solution was cooled to 0° and drained into a tared, cooled, polyethylene bottle, weighed and stored at −30° C. The solution weighed 75.1 grams (85% yield).

At a 10.0 weight percent loading, the above solution cured the unsaturated polyester-styrene resin of Example III at room temperature giving a peak exotherm of 260° F. (127° C.) in 14.8 minutes and a hard cured resin which was water white in color.

In the polymerization of vinyl chloride (8 hours at 50° C.) using the procedure described in Example IV, it was found that .0270 grams of 2-cyclohexylazo-2-hydroperoxypropane were required per 100 grams of vinyl chloride monomer to obtain a 90% conversion to polyvinyl chloride.

EXAMPLE XVII

Preparation of Sodium 2-t-Butylazo-isopropylhydroperoxide

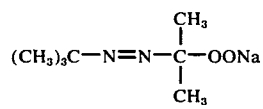

METHOD A

To a slurry of 2.31 grams (.055 moles) of 57% sodium hydride (in mineral oil) in 100 ml. of pentane in a 200 ml. 4 neck flask equipped with a magnetic stirrer, thermometer, addition funnel and gas bubbler, was added 16.25 grams (.055 moles) of a 54.5% pentane solution of 2-t-butylazo-2-hydroperoxypropane dropwise and with rapid stirring. The temperature was held at 0°–5° C. during the addition and the 2-t-butylazo-2-hydroperoxypropane solution was not allowed to warm up above 10° C. during the addition. After the addition was complete, the reaction was stirred for an additional 40 minutes at 0° C. At this point hydrogen evolution had ceased indicating the reaction was done. Attempts to isolate the salt by filtration or by evaporation of the solvent under reduced pressure at 0° C. led to decomposition of the very unstable salt.

METHOD B

To 22.0 grams (.055 moles) of a 10% sodium hydroxide solution cooled to 0° C. was added 16.25 grams (.055 moles) of a 54.5% solution of 2-t-butylazo-2-hydroperoxypropane dropwise and with rapid stirring over a 10 minute period. The temperature was held at 0° C. during the addition and the 2-t-butylazo-2-hydroperoxypropane solution was not allowed to warm up above 10° C. during the addition. After the addition was complete, the reaction was stirred for 2 hours at 0° to 5° C. The salt was a white solid. A 50 ml. portion of ice cold water was added to dissolve the salt. The mixture was then extracted with pentane. The aqueous solution of sodium 2-t-butylazo-isopropylhydroperoxide was separated and refrigerated at 5° C. The pentane layer was dried over anhydrous sodium sulfate, filtered and the solvent evaporated at 0° C. under reduced pressure to leave 1.2 grams (13.6%) of unreacted 2-t-butylazo-2-hydroperoxypropane.

The aqueous solution was then cooled to 0° C. and 60 ml. of pentane was added. The mixture was then acidified with dilute HCl to a pH of 4. The pentane layer was separated and washed with H₂O, dried over anhydrous sodium sulfate, filtered and the solvent evaporated at 0°

EXAMPLE XVIII

Preparation of Potassium 2-t-Butylazo-isopropylhydroperoxide

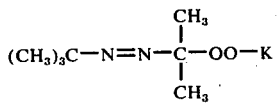

To 15.4 grams (.0275 moles) of a 10% potassium hydroxide solution cooled to 0° C was added 8.12 grams (.0275 moles) of a 54.5% solution of 2-t-butylazo-2-hydroperoxypropane in pentane dropwise and with rapid stirring. The temperature was held at 0° C. during the addition and the 2-t-butylazo-2-hydroperoxypropane solution was not allowed to warm up above 10° C. during the addition. After the addition was complete, the reaction was stirred for 2½ hours at 0° to 5° C. The aqueous mixture was extracted with pentane. The aqueous solution of potassium 2-t-butylazo-isopropylhydroperoxide was separated and refrigerated at 5° C. The pentane layer was dried over anhydrous sodium sulfate, filtered and the solvent evaporated at 0° C. under reduced pressure to leave 1.2 grams (27.2%) of unreacted hydroperoxide. The aqueous solution was cooled in an ice bath and 50 ml. of pentane added. The mixture was acidified to pH 4 with dilute HCl to convert the potassium salt back to the free hydroperoxide. The pentane layer was separated and washed with water, dried over anhydrous sodium sulfate, filtered and stripped. The residue weighed 3.0 grams indicating that 93% of the potassium salt was recovered.

EXAMPLE XIX

Preparation of the Sodium Salt of 2-t-Butylazo-2-hydroperoxy-4-methylpentane

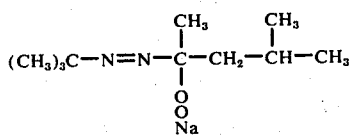

To a slurry of 0.95 grams (.0224 moles) of 57% sodium hydride (in mineral oil) in 50 ml. of pentane in a 100 ml. 4 neck flask equipped with a magnetic stirrer, thermometer, addition funnel and gas bubbler, was added 9.0 grams (.0224 moles) of a 50% solution of 2-t-butylazo-2-hydroperoxy-4-methylpentane in odorless mineral spirits. The solution was added dropwise and with rapid stirring, holding the temperature of the reaction mixture at 0°–5° C. and not allowing the temperature of the azo-hydroperoxide solution in the dropping funnel to rise above 10° C. After the addition was complete (15 minutes), the reaction was stirred for an additional 30 minutes at 0° to 5° C. At this point hydrogen evolution had ceased indicating the reaction was complete. The reaction mixture was filtered on a precooled filter and sucked dry on the filter. The filter cake was then transferred to a beaker cooled in dry ice. The salt almost immediately decomposed, evolving a white smoke.

EXAMPLE XX

Preparation of the Sodium Salt of 1-t-Butylazo-1-hydroperoxycyclohexane

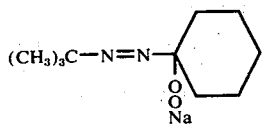

To a slurry of 1.05 grams (.025 moles) of 57% sodium hydride (in mineral oil) in 50 ml. of pentane in a 100 ml. 4 neck flask equipped with a magnetic stirrer, thermometer, addition funnel and gas bubbler, was added 10.0 grams (.025 moles) of a 50% solution of 1-t-butylazo-1-hydroperoxycyclohexane in odorless mineral spirits. The solution was added dropwise and with rapid stirring, holding the temperature of the reaction mixture at 0°–5° C. and not allowing the temperature of the azo-hydroperoxide solution in the dropping funnel to rise above 10° C. After the addition was complete (15 minutes), the reaction was stirred for an additional 30 minutes at 0° to 5° C. At this point hydrogen evolution had ceased indicating the reaction was complete. The reaction mixture was filtered on a precooled filter and sucked dry on the filter. The filter cake was then transferred to a precooled, tared beaker and weighed. The salt weighed 5.0 grams (90% yield) and was stable at dry ice temperatures. The salt decomposes when allowed to stand at room temperature. It is mildly shock sensitive (smokes at 10 inches on the duPont tester).

What is claimed is:

1. A compound of the formula

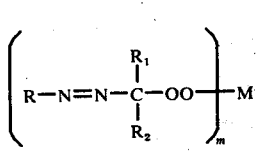

where M is hydrogen, alkali metal or alkaline earth metal; m is the valence of M;
R is $C_1 - C_{12}$ alkyl, $C_3 - C_{12}$ cyclo-, bicyclo- or tricycloalkyl, or $C_7 - C_9$ aralkyl;
$R_1$ and $R_2$ are separately selected from hydrogen, $C_1 - C_8$ alkyl, $C_3 - C_{12}$ cyclo-, bicyclo- or tricycloalkyl, $C_7 - C_{12}$ aralkyl, and $C_6 - C_{14}$ aryl;
and $R_1$ and $R_2$ taken together form $C_3 - C_7$ alkylene; and one or more of each of R, $R_1$ and $R_2$ can be substituted with lower alkoxy, hydroxy, carboxy, lower alkoxycarbonyl, lower alkylcarbonyloxy, halogen, cyano, dimethylamido or lower alkylsulfonato.

2. A compound as in Claim 1 where R, $R_1$ and $R_2$ are unsubstituted.

3. A compound as in claim 2 where M is hydrogen, sodium or potassium; m is 1; R is $C_1 - C_{12}$ alkyl; and $R_1$ and $R_2$ are $C_1 - C_8$ alkyl or join to form $C_3 - C_7$ alkylene.

4. 2-t-Butylazo-2-hydroperoxy-4-methylpentane.
5. 2-t-Butylazo-2-hydroperoxyoctane.
6. 1-t-Butylazo-1-hydroperoxycyclohexane.
7. 2-methylazo-2-hydroperoxy-4-methylpentane.
8. Potassium 2-t-butylazo-isopropylhydroperoxide.
9. Sodium salt of 1-t-Butylazo-1-hydroperoxycyclohexane.

* * * * *